United States Patent [19]

Stawitcke et al.

[11] 4,448,192

[45] May 15, 1984

[54] MEDICAL VENTILATOR DEVICE PARAMETRICALLY CONTROLLED FOR PATIENT VENTILATION

[75] Inventors: Frederick A. Stawitcke; William J. Mordan, both of Sunnyvale; Holly B. Jimison, Palo Alto; Robert Piziali, Stanford; Allen K. Ream, Woodside, all of Calif.

[73] Assignee: Hewlett Packard Company, Palo Alto, Calif.

[21] Appl. No.: 354,993

[22] Filed: Mar. 5, 1982

[51] Int. Cl.³ ............................................ A61M 16/00
[52] U.S. Cl. ................................................ 128/204.26
[58] Field of Search ...................... 128/204.21, 204.23, 128/204.24, 204.25, 204.26, 205.13, 205.14, 205.15, 205.18

[56] References Cited

U.S. PATENT DOCUMENTS

| | | | |
|---|---|---|---|
| 3,741,208 | 6/1973 | Jonsson et al. | 128/204.21 |
| 3,817,246 | 6/1974 | Wiegl | 128/204.24 |
| 3,961,627 | 6/1976 | Ernst et al. | 128/204.21 |
| 3,972,327 | 8/1976 | Ernst et al. | 128/204.21 |
| 4,036,221 | 7/1977 | Hillsman et al. | 128/204.21 |
| 4,256,100 | 3/1981 | Levy et al. | 128/204.21 |
| 4,265,237 | 5/1981 | Schwanbom et al. | 128/204.25 |
| 4,393,869 | 7/1983 | Boyarsky | 128/204.21 |

FOREIGN PATENT DOCUMENTS 2314356  3/1973  Fed. Rep. of Germany ........................ 128/204.23

OTHER PUBLICATIONS

Wald et al., "A Computers System for Respiratory Parameters," *Comp. and Biomed Res.*, vol. 2, pp. 411-429 (1969).
Drebes et al., "Interval Estimation of Respiratory Parameters Using Least Squares Techniques," *Compound Biomed Res.*, vol. 12, pp. 149-166 (1979).
Kolff et al., "Electrical Analogues of Methods for Continuous Postive-Pressure Ventilation," *J. of Thoracic and Cardiovascular Surg.*, vol. 64, No. 4, Oct. 72, pp. 586-591.
Lorino et al., "Linear Modeling of Ventilatory Mechanics During Spontaneous Breathing," *Comp. and Biomed Res.*, vol. 15, pp. 129-144 (1982).
Harries et al., "Mechanical Assistance to Respiration in Emphysema," *Am. J. of Med.*, vol. 36, Jan. 1964, pp. 68-78.
Otis et al., "Mechanical Factors in Distribution of Pulmonary Ventilation," *J. of Applied Physiology*, vol. 8, Jan. 1956, pp. 427-442.
Jain et al., "A Control System for Long-Term Ventilation of the Lungs," *IEEE Transactions on Biomedical Engineering*, vol. BME-19, No. 1 (Jan. 72), pp. 47-53.
Woo et al., "Lyapunov Redesign of Model Reference Adaptive Control System for Long Term Ventilation of Lung," *ISA Transactions*, vol. 14, No. 1, (1975), pp. 89-98.
Woo et al., "Digital Simulation of an Adaptive System for Long-Term Ventilation of the Lungs," *IEEE Transactions on Biomedical Engineering*, vol. BME-20, (Nov. 73), pp. 475-477.

*Primary Examiner*—William E. Kamm
*Assistant Examiner*—Mitchell J. Shein
*Attorney, Agent, or Firm*—Edward Y. Wong

[57] ABSTRACT

A ventilator which accommodates to a patient's efforts in breathing and to his change in respiratory requirements is provided by a system with a novel control law. The novel control law determines a target ideal pressure-volume wave-form which characterizes the patient's respiratory requirements; this waveform is constantly modified and corrected during the course of ventilator operation to enable the patient to breathe with minimum ventilation opposition, or fighting.

9 Claims, 17 Drawing Figures

MEDICAL VENTILATOR DEVICE PARAMETRICALLY CONTROLLED FOR PATIENT VENTILATION

BACKGROUND OF THE INVENTION

When normal breathing is impaired for a patient, either because of pathological problems with the patient's lungs, such as high airway resistance or lung stiffness, or because of other extra-pulmonary physiological problems, such as paralysis due to poliomyelitis, head injuries, and the like which prevent the patient from maintaining proper respiration, a mechanical system that aids the patient in breathing is generally required. A ventilator that supplies and/or withdraws respiration gas to and from the patient is such a system. To be truly effective in supplying gas, a ventilator generally needs a prescription to adapt the ventilation to suit the particular patient. This ventilator prescription is supplied by a clinician.

A ventilator prescription by a clinician involves selecting, inter alia, an initial tidal volume, flow rate (and hence inhale time), inhale pause time, and exhale time. After the initial selection, fine adjustments, largely based on subsequent blood gas measurements, are made to these initial selections. Breathing rate and minute ventilation may be computed from these parameters. If the adjustments are properly made, some patient interaction with the ventilator is possible. For example, the proper setting of triggering sensitivity and upper pressure limit allows the patient some control over the ventilator's operation. Such patient accommodation, though difficult to achieve in a ventilator, especially those in the prior art, is highly desirable.

In prior ventilation art, inhalation delivery appears to be controlled by a time-dependent function only. These conventional ventilators generate either flow, and hence volume, or pressure as a constant or time-dependent waveform during inhalation. Therefore these ventilators can be categorized as a volume ventilator or a pressure ventilator.

The pressure ventilator is characterized by a system that terminates inhalation when a preset pressure limit is reached. In contrast, the volume ventilator is characterized by a system that terminates inhalation when a preset volume is reached, volume being flow in a finite time period. There are also time-cycled ventilators, which in general are functionally equivalent to one of the above two types.

Common to these prior art ventilators are the mechanisms for transfer of air. The positive transference of air, or delivery of air, is generally provided by one of two types of mechanisms: a pressurized reservoir or a positive displacement pump. Depending upon the method of implementation, either of these may deliver air at a predetermined flow rate or at a flow rate determined by the pressure at the airway opening.

Another feature common to most ventilators is a mechanism in the cycling logic known as triggering. At the end of exhalation, air pressure in the tubing which is below a normal minimum value is detected. This detection in turn causes an early initiation of the next inspiratory cycle. This triggering feature is adjustable to make it less susceptible to pressure artifacts.

A prime concern of any ventilator is accommodation to patient effort. Accommodation to patient effort, or control by the patient, is defined primarily as synchronization of the ventilator's inhale and exhale phases with the phases of the patient's efforts. Secondarily it means the ability to deliver air at the rate desired by the patient. In other words, the ventilator with patient effort accommodation allows the patient some control over the ventilator's operation. Such patient effort accommodation in the ventilators in the prior art, however, is achieved, if at all, only with great difficulty. In contrast, the present invention achieves an accommodation to patient effort not only superior to but also easier than that in prior art ventilators. The ventilator in accordance with the present invention accomplishes this by employing a novel pressure-volume control law. One beneficial result of accommodating patient effort is to mitigate the frequently traumatic process of initiating mechanical ventilation. For example, through augmentation of the patient's efforts and gradually increasing the tidal volume and slowing the rate to that preset on the ventilator, the patient can be made to relax and allow his ventilatory pattern to be synchronous with that of the ventilator.

If a ventilator control law completely ignores the patient's attempts to control breathing, as in the case with prior art ventilators not having patient effort accommodation, ventilation fighting occurs. This fighting, unfortunately, is often expediently resolved by simply reducing the patient's drive to breathe, such as by heavy sedation. This expediency leads to the necessity of intense monitoring of the ventilated patient to ensure that the controlled ventilation remains appropriate. Both the fighting and the means to control it in the prior art are usually unsatisfactory and have undesirable side effects that impair the patient's recovery. The ventilator using a pressure-volume control law in accordance with the invention overcomes these undesirable side effects.

In addition to the lack of satisfactorily controlling fighting, the prior art ventilators have other attributes that also contribute to unsatisfactory performance. One great contributor is the transducers used in measuring the flow of the respiration gas to and from the patient. It is necessary to monitor flow to determine airway resistance and lung compliance and to servo control the flow of air to or from the patient. Ventilators in the prior art often use flow transducers to do this monitoring of flow. For accurate measurements in such systems, the flow transducer is positioned close to the patient's airway; however, water vapor or sputum in the patient's airway tends to clog or otherwise compromise the accuracy of the flow measurements. Flow transducers thus are susceptible to error. This is especially a problem on the negative transference, or exhale, side of the circuit.

In the prior art ventilators, exhalation regulation has also been unsatisfactory. Other than providing an optional variable end-expiratory pressure or mechanical retardation, these ventilators do not really regulate exhalation. A two-phase pressure control method for regulating exhalation has been disclosed in the prior art in U.S. Pat. No. 3,961,627, entitled "Automatic Regulation of Respirators" and issued to Ernst et al. However, with this method pressure is controlled as a function of time, so that when flow rate varies, the optimal back pressure is not attained. For example, optimal back pressures for certain diseases, such as emphysema, are dependent on lung volume. Therefore, in such cases, regulation with time as the independent variable is highly undesirable.

Still another area of unsatisfactory performance in the prior art ventilators is in the handling of a cough. When a patient coughs, his respiratory requirements change immediately. Since a cough is a complex, highly coordinated act that results in the rapid expulsion of alveolar gas at a very high velocity, the cough requires a spontaneous reaction in the ventilator to account for it. Although the cough is useful in sweeping the airway free of irritant gases, dust, smoke, excess mucus, cell debris or pus, it can be problematic. For example, the patient develops high intrathoracic and intrapulmonic pressures with a forced expiratory effort against a closed glottis during a cough. The glottis then opens abruptly so that there is a large difference between alveolar pressure and upper tracheal pressure. This results in a very large flow rate for the cough. The compression of the intrathoracic airways due to high intrathoracic pressures also increases the gas velocity. However, a prior art ventilator typically interferes with this coughing process. Because tubing prevents the constriction of the glottis during a cough, an intubated patient on a prior art ventilator will not be able to cough effectively. Manual suctioning of the airway using a catheter must then be performed on the patient. However, suctioning is generally only effective in a limited distribution of the airways; it is also traumatic to the airway mucosa. Atelectasis and severe acute circulatory disturbances may occur during suctioning, because the catheter connects the interior of the trachea to the wall suctioning. Furthermore, the catheter can also occlude the endotracheal tube through which it passes. Profound hypoxia, vagal stimulation, acute right-heart strain and left-heart loading can accompany the very low lung volumes and intrathoracic pressures which will result from suctioning. All this can be avoided with the preferred embodiment that can provide an artificial cough.

Another disadvantage in the prior art ventilators is the difficulty in weaning the patient from a ventilator. In the normal course of events, all patients eventually must make the transition from ventilator support to spontaneous breathing. During this transition or weaning period, conflicts usually arise between the patient's and the ventilator's control systems. The patient may be making transient or irregular efforts such as sighing or coughing, or he may be making a sustained effort to increase the tidal volume and/or breathing rate. For most patients, these efforts to resume control of respiration are considered desirable by the clinician. Conflicts occur because, for most patients, the ability to resume regulation of breathing precedes the resumption of the ability to do the work of breathing. Respiratory muscle augmentation is still needed, but the prior art ventilator's inflexible, time-dependent control system cannot permit the patient to control the pattern of breathing.

In prior ventilation art, variable assistance provided by the ventilator is controlled using intermittent mandatory ventilation (IMV). A gas source is provided to the patient for spontaneous breathing, and the ventilator provides controlled breaths intermittently. The rate of controlled breaths and the tidal volume is variable, usually as a selectable setting. In some systems the mandatory breaths can be patient-initiated. This is termed synchronous IMV, or SIMV. The patient-initiated breaths are not necessarily more physiological in nature or more comfortable to the patient, because it requires developing significant negative pressures without reversed air flow to initiate them. Furthermore, intermittent mandatory ventilation in the prior art generally has the disadvantage of unexpectedly delivering an occasional forced assistance.

SUMMARY OF THE INVENTION

Figure 1:
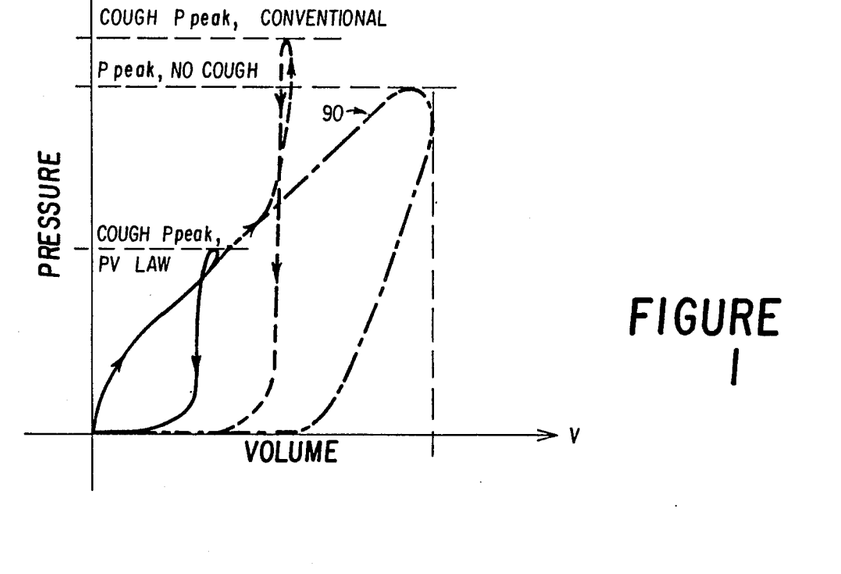
FIG. 1 shows the improvement of accommodating to a patient's breathing with the ventilator in accordance with the invention.
Figure 2:
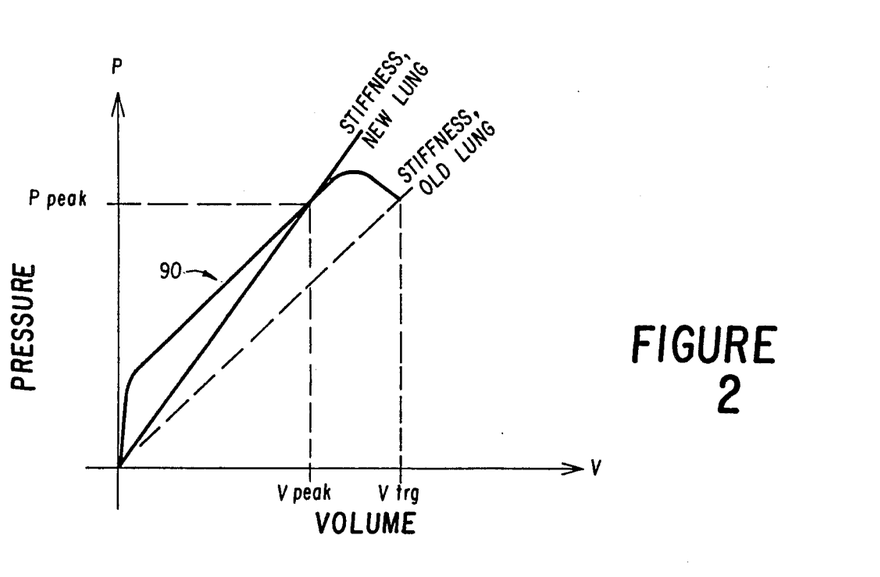
FIGS. 2 and 3 show updating of a target pressure to accommodate a patient's changing respiratory requirements.
Figure 3:
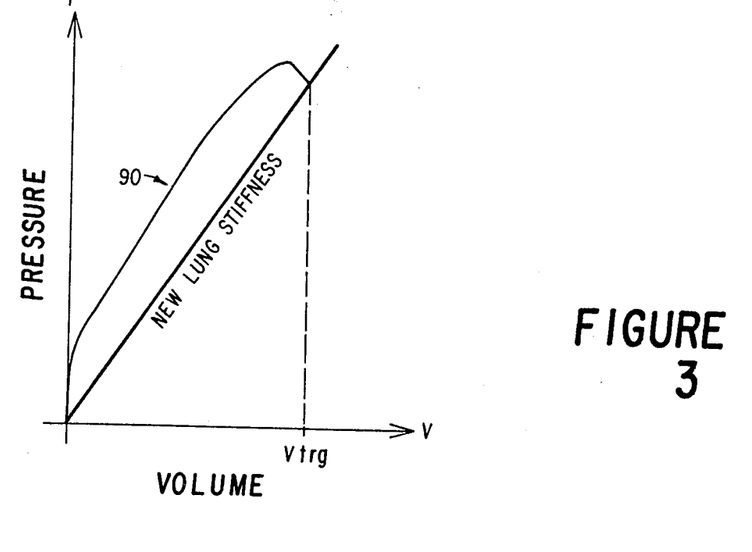

The present invention provides a method for reguating ventilation to a patient by using parametric control laws for regulating pressure as a function of volume for inhale and exhale. This is in contrast to the general method in the prior art which controls pressure or flow as a function of time. The new type of control provides easy patient interaction during a breath; it also ensures that the airway pressures are appropriate for the patient's activity at substantially all times. For example, if the patient coughs during inhale the regulated pressure will change only according to the inhale pressure-volume control law unless patient-initiated switching from inhale to exhale occurs. At that point, pressures follow an exhale control law. Thus, if the patient resists air delivery and prevents preset amounts from being delivered, the patient has also prevented the application of maximum delivery pressures. Unnecessarily high pressures are prevented by this novel fundamental control method rather than by auxiliary pressure detection and subsequent pressure relief by the opening of a pressure relief valve. This is graphically shown in FIG. 1. This is one advantage of the present invention. Another advantage is that when changes in lung compliance or airway resistance are detected, the control law is automatically adapted so that the correct pressures are given to achieve the required tidal volume. This is illustrated in FIGS. 2 and 3.

The preferred embodiment of the present invention is an electrically powered and controlled ventilator from which the ventilating gas is supplied to the patient through a single circuit by a linearly driven piston with a rolling bellows diaphram. Piston position, which directly gives actual volume information, is continuously monitored. The information thus derived is used along with system pressures and, possibly, temperatures to further derive airway gas flow. In this manner, the need for a flow transducer, which has inherent disadvantages as described earlier, is obviated.

A second preferred embodiment includes an exhale piston in addition to the inhale piston. The exhale piston position, and hence gas volume, and gas pressure are also continuously monitored. This allows greater accuracy of volumetric monitoring than through prior art methods requiring the use of flow transducers. Furthermore, this exhale information, if desired, can be visually displayed as waveforms and closely monitored or controlled.

The present invention controls airway pressure during exhalation. This makes it possible to relieve the sensation of breathing against the airway resistance of the tubing. As is the case with the inhale control law, the exhale control law also regulates pressure as a function of volume. This allows empirical determination of control law parameters as a function of lung volume to result in shortest exhalation times in the presence of certain diseases, like emphysema. This allows for a more precise and continuous accommodation of the patient's respiratory needs.

Another aspect of the present invention is the option of an artificial cough. In the preferred embodiment this is made available as a manual pushbutton control to provide an alternative to suctioning with a catheter. A sigh, which is a larger-than-normal breath, normally precedes the artificial cough. At the point of expiration, a negative pressure-volume control law is employed to enhance the expiratory flow until the previously-delivered volume is removed.

An additional preferred embodiment includes a novel provision for ensuring target ventilation when a patient actively resists the delivery from the ventilator. The method for this involves detecting patient activity by noting early inhale-to-exhale switching or large intra-breath variations in inhale flow. The pressure-volume control law is not modified by the adaptor for breaths with significant patient activity. For those breaths where patient activity causes the delivered volume to be under target, the control law for the next breath is modified in the following way. A variable controlled resistance is added to the inhale control law by regulating pressure as a function of flow as well as volume. This novel control of added artificial resistance can enhance or reduce the resistive sensation associated with the tubing between the ventilator and patient. The pressure required for active inhale-to-exhale switching is also increased in proportion to the additional artificial resistance. This effectively adds another dimension to the preferred embodiment to make it progressively more difficult for the patient to continue to actively modify the delivery of ventilation after low-volume, patient-resisted breaths.

Figure 10A:
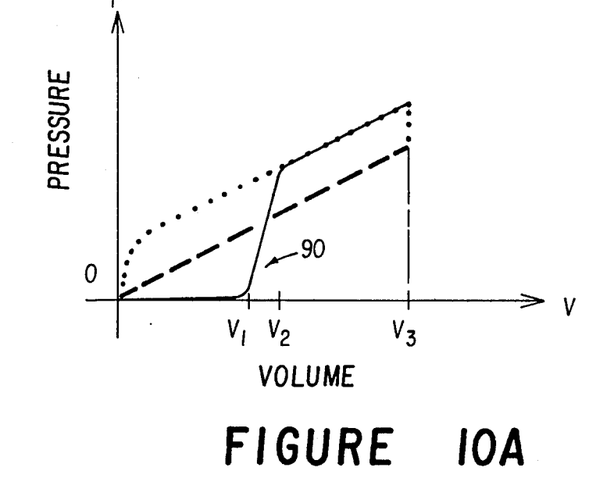
FIGS. 10A and 10B show waveforms representing a pressure-volume control law and volume varying with time for partial assistance, respectively.
Figure 10B:
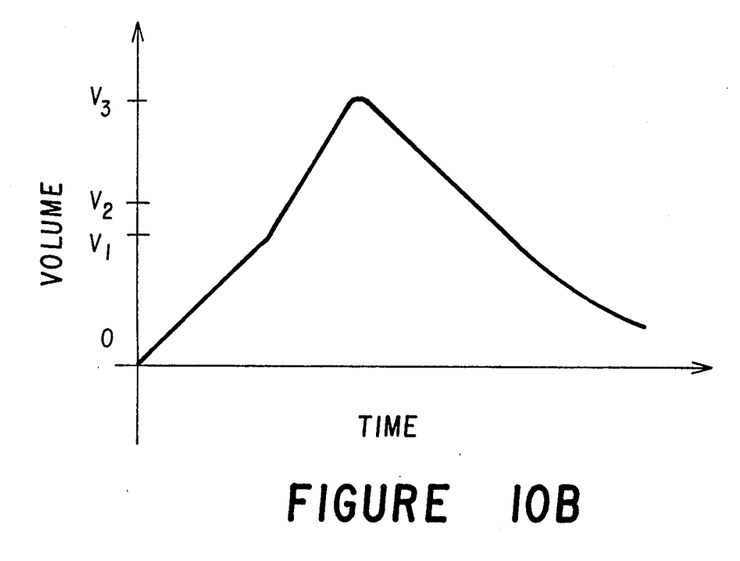

The preferred embodiment of the invention also makes available a novel method of providing partial assistance to be used as a mode of therapy or for weaning patients from a ventilator. The assistance is provided at the end of each breath initiated by the patient. The amount of assistance is either set by the clinician or automatically optimized by the ventilator; this amount determines the fraction of the required tidal volume to be delivered by the ventilator after the complementary volume has been actively inspired by the patient. A volume-versus-time waveform and a pressure-volume control law for this mode of partially assisted ventilation are shown in FIGS. 10A and 10B.

Figure 11A:
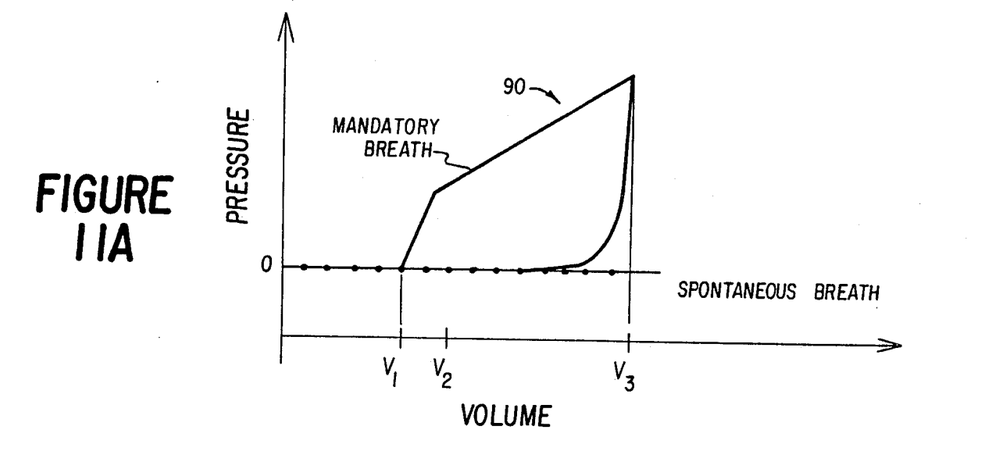
FIGS. 11A–11C show waveforms representing a pressure-volume control law and volume and pressure varying with time for partially assisted SIMV, respectively.
Figure 11B:
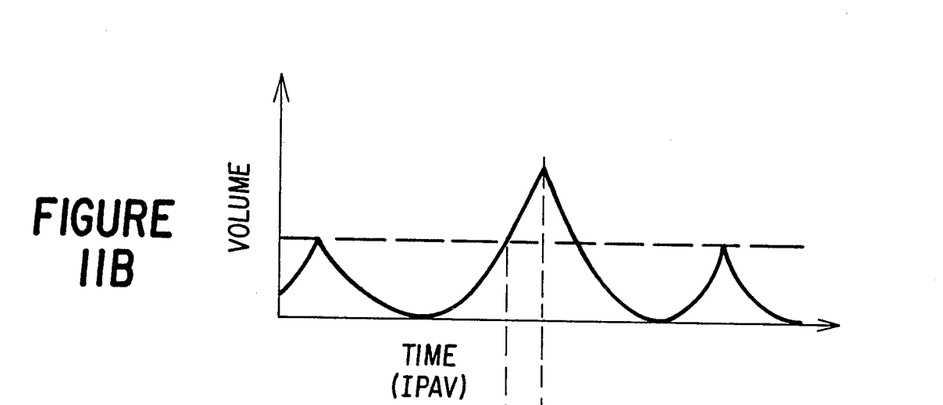
Figure 11C:
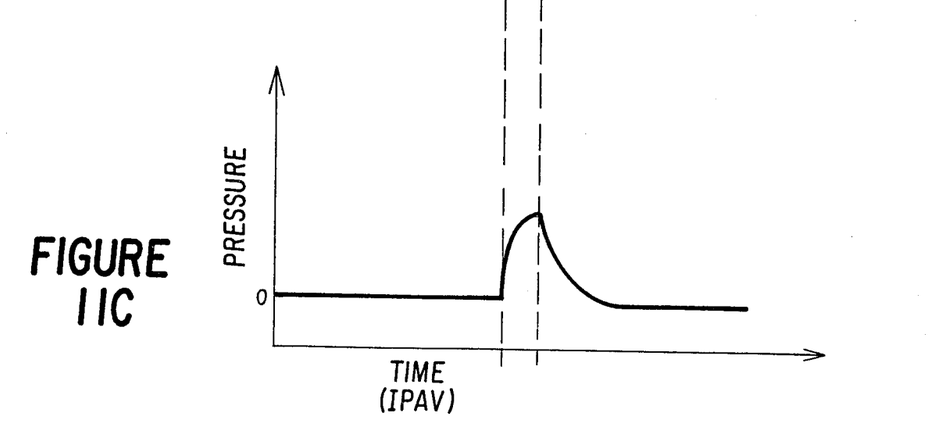

A further variation of this novel mode of ventilation is to partially assist the mandatory breaths in synchronized intermittent mandatory ventilation. Spontaneous breaths are provided with a control law that maintains air delivery pressure equal to the ambient atmospheric pressure for all volumes. A running average of spontaneous tidal volumes is maintained to determine the point in the mandatory breath where the positive pressure control laws are to start. The mandatory breaths are controlled in a manner similar to the partially assisted breaths described earlier, but with the degree of assistance determined by average spontaneous tidal volume instead of a clinician's percent assistance setting. A graphical description of this is shown in FIGS. 11A–11C.

Partially assisting every breath has the advantage of allowing the patient to gradually take over the work of breathing in a more physiological manner than intermittent mandatory ventilation, since it is not necessary to have occasional, unexpected large breaths. Another advantage of this new mode of partial assistance is that a separate breathing circuit is not required; the partial assistance circuit is the same as the full assistance circuit. The parametric control is altered to provide partial assistance. Furthermore, the new mode of partial assistance in accordance with the invention starts each breath with negative intrathoracic pressures. With negative intrathoracic pressure breathing, air flows into the lungs spontaneously. It has been found that negative pressure breathing improves the distribution of gases in the lungs as compared to positive pressure breathing, or controlled ventilation. The improvement is due to better matching of ventilation to perfusion. Thus, the new mode of partial assistance of starting each breath with negative intrathoracic pressures adds another advantageous dimension to partial assistance ventilation.

DETAILED DESCRIPTION OF THE INVENTION

Illustrated Embodiment

Figure 4:
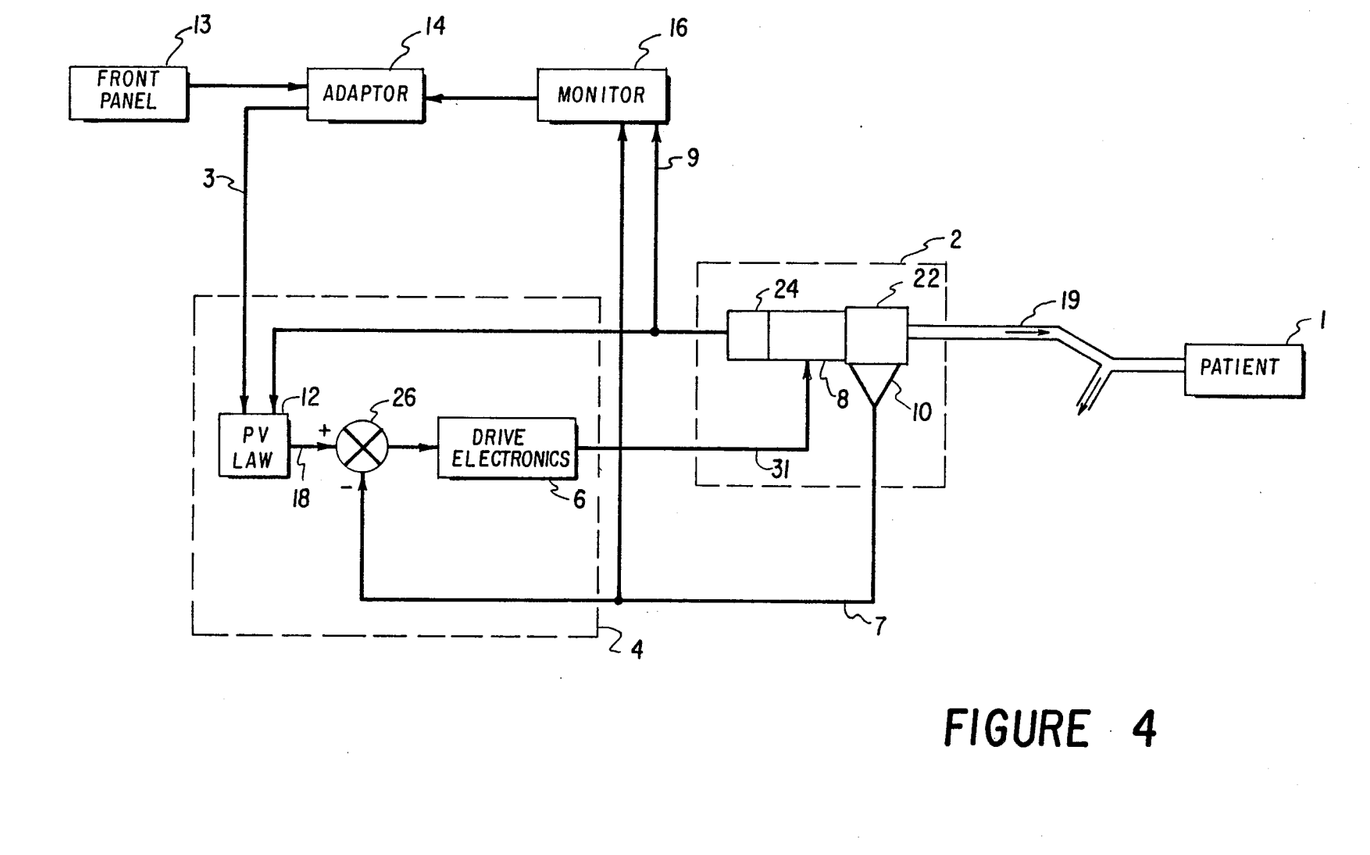
FIG. 4 is a simplified block diagram of the ventilator in accordance with the preferred embodiment of the invention.

One simplified embodiment of the ventilator in accordance with the invention has, as illustrated in FIG. 4, a respiratory gas source 2 controlled electronically by a regulator 4. The regulator 4 is a closed-loop system. It has, inter alia, a pressure target generator 12, a pressure comparator 26, and servo compensation and drive electronics 6. The output of the regulator 4 is a motor drive current 31, which drives a piston motor 8 to control the amount of respiratory gas the source 2, or more specifically, the inhale air delivery mechanism 22 in the source 2, is to supply the patient. The electronics 6 act in response to a comparison of the actual respiratory pressure in the inhale delivery mechanism. A pressure comparator 26 makes this comparison from the data from a pressure transducer 10 and that idealized by a pressure-volume controller 12. This controller 12 follows a novel pressure-volume control law to be more fully described below. By taking into consideration the momentary volume of respiratory gas being supplied to the patient and the desired volume waveform prescribed by the clinician, a proper pressure-volume waveform 90 of the respiration gas for the patient is precisely characterized by an adaptor unit 14 and is relayed to the controller 12. The controller 12 takes this pressure-volume waveform and derives a target pressure 18 according to this waveform and the measured piston position signal 9. It is the adaptor unit 14 which constantly computes a proper pressure-volume waveform for the patient, depending on the actual parameters contained in the monitor 16 and prescribed by the clinician via the front panel 13, that enables the controller 12 to adapt to the patient's varying respiratory requirements.

Figure 5:
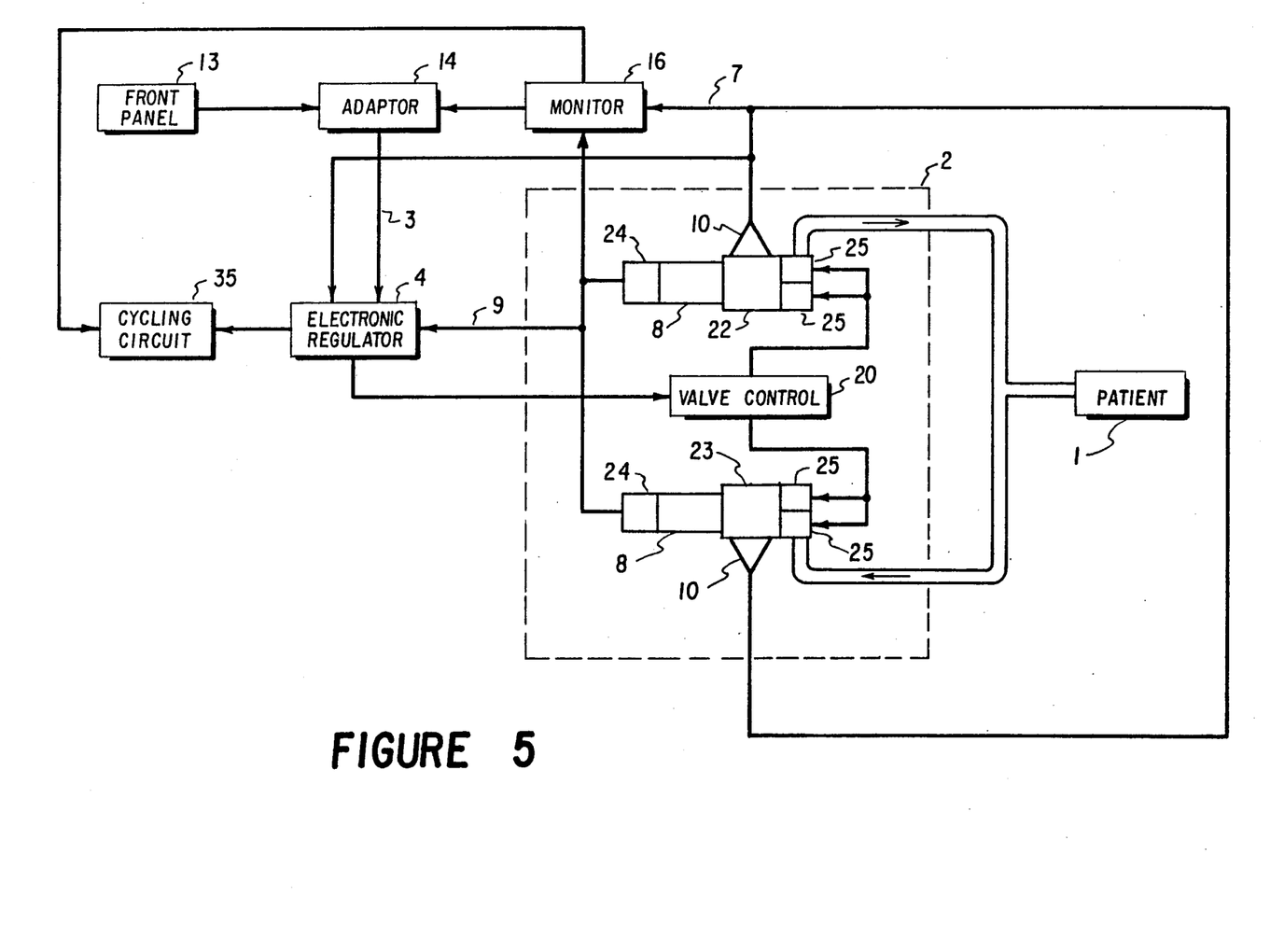
FIG. 5 shows the ventilator in accordance with the preferred embodiment of the invention.
Figure 9:
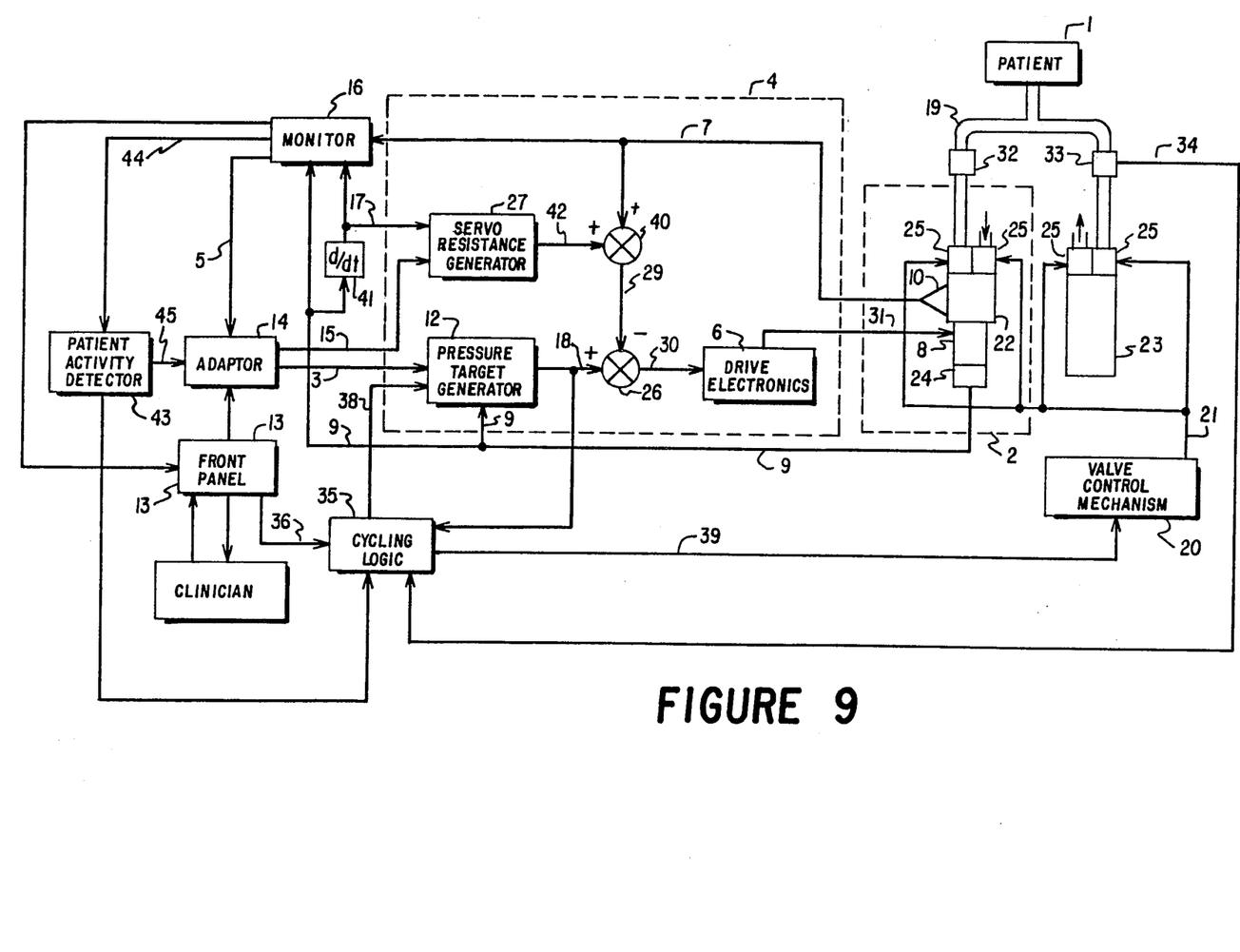
FIG. 9 shows a detailed schematic of the preferred embodiment including a pressure servo for providing additional artificial resistance.

FIGS. 5 and 9 detail the ventilator in accordance with the preferred embodiment of the present invention more fully. Therein, a complete ventilator having facilities for supplying as well as for withdrawing respiratory gas to and from a patient is depicted. Systems having facilities only for supplying respiration gas, such as in FIG. 4, or only for withdrawing respiration gas are alternate embodiments of the present invention. In FIG. 5 the respiration gas source 2 has an inhale piston 22 for supplying respiration gas and an exhale piston 23 for withdrawing such gas. In this latter instance, the respiration gas source 2 can be considered a negative source when gas is being withdrawn. Determining the actual volumes being supplied or withdrawn are shaft encoders 24. By determining the precise position of these pistons 22-23, the volume therein is known. This information is collected in a monitor 16 via a line 9; it is also relayed to an electronics regulator 4 through line 9. A clinician prescribes certain goals for the ventilator, depending on the physical condition of the patient. These goals are entered into a front panel 13, which relays them to a cycling logic circuit 35 and an adaptor unit 14. The adaptor unit 14 formulates the proper pressure-volume waveform in accordance with the novel pressure-volume control law, and the regulator 4 follows it in controlling the respirator gas source 2. The cycling circuit 35 controls a set of solenoid valves 25 through a valve control mechanism 20. At the proper transition times for inhalation to exhalation, and vice versa, the cycling logic circuit 35 switches the proper valves 25 to connect the appropriate inhale line for supplied gas and exhale line for withdrawn gas.

Since data on the actual conditions of the patient are collected and entered into the adaptor unit 14 via the monitor unit 16, the adaptor unit 14, by using the novel pressure-volume control law, can maintain a continuously up-to-date pressure-volume waveform that truly reflects the requirements of a patient. This is made evident by the following discussion.

Theory of Pressure-Volume Control Law

In the illustrated embodiment of the invention in FIG. 9, the parametric control law is a pressure-volume (PV) control law, which controls ventilator pressure as a function of the volume of air delivered. One form of the law, specifically designed to provide a constant air flow rate during the inhale phase of breathing, is:

$$\text{Pressure} = A \times \text{Volume} + B. \tag{1}$$

The first term on the right, $A \times \text{Volume}$, generates a pressure which increases with delivered volume to offset the elastic recoil of the lung and thorax. The second term, B, is a constant that offsets the flow resistance of the airways, thus causing a constant rate of flow of air into the lungs.

Generating pressure as a function of volume gives the patient considerable control over the flow profile within each breath. The first term in Equation 1 offsets elastic recoil without regard to elapsed time or air flow rate. The flow rate will then result from the sum of the second term and any breathing effort the patient makes. This results in a constant relationship between the level of patient effort and the resulting change in the flow rate. When the effort ceases, the flow rate returns to its previous value.

When the patient makes an expiratory effort large enough to halt the air delivery, a non-return valve 32 in the delivery tubing prevents reverse flow that would contaminate the ventilator's air supply system. Equation 1 guarantees that air pressure upstream of the valve ceases to rise. The patient can cause the ventilator to switch to the exhalation phase by raising the airway pressure above the pressure in the ventilator by an adjustable threshold amount. The level of effort required to cause switching is constant, regardless of elapsed time or volume delivered.

In the absence of patient effort, the inhalation phase ends when the preset inhale time limit is reached. If the delivered volume reaches the preset value, Vtrg, or target volume, before the time limit, the pressure law is modified to:

$$\text{Pressure} = A \times V_{trg}. \tag{2}$$

This value, though sufficient to offset the elastic recoil of the lungs at the target volume, does not provide any additional air flow. If the patient makes an inspiratory effort beyond this volume, he will receive additional air while pressure is held constant at the level of Equation 2. Delivery requirements are maintained by adjusting the coefficients A and B in Equations 1 and 2 to match changes in the patient's elastic recoil or airway resistance. Breathing efforts by the patient may also cause the apparent values of these parameters to change. The coefficient A is adjusted until the flow rate during the course of the breath is neither increasing nor decreasing, that is, constant in a statistical sense. The coefficient B is adjusted until the average value of the flow rate is correct. In this way patient accommodation is achieved in the short term, while the delivery goals are met in the long term.

In the illustrated embodiment, the ventilator in accordance with these principles provides accommodation of a predetermined magnitude to the patient's efforts, regardless of the volume of air delivered, and permits the patient 1 to switch from the inhale to the exhale phase before the normal cycling occurs. The ventilator has a nonreturn valve 32 to prevent a reverse flow of air from the patient 1 to the delivery mechanism 22. This is accomplished by having an airway pressure transducer 33 to provide an airway pressure signal 34 for a cycling logic circuit 35, which compares the pressure signal 34 with the pressure target signal 18. The cycling logic circuit 35 produces a pressure difference in the comparison. This difference is compared in turn to a selected threshold pressure difference 36 emanating from a front panel 13; if it exceeds this threshold, a phase signal 38 is produced to cause a forced phase transition, that is, the inhale phase is switched to the exhale phase. The cycling logic circuit 35 sends the phase signal 38, when present, to the pressure target generator 12 in order to terminate the inhale phase of the pressure target generation. Simultaneously, the cycling logic circuit 35 also sends valve commands 39 to a valve control mechanism 20, which in turn sends appropriate valve control commands 21 to air control valves 25 to disconnect the inhale air delivery mechanism 22 and to connect an exhale air receiving mechanism 23 to the patient 1 for the exhale phase.

From the above discussions, Equation 1 can be rewritten in the following form:

$$Pressure = V/Ch + Rh \times Fd, \quad (3)$$

where: V is the Volume; Ch is the estimated lung compliance, and $Ch = 1/A$; Rh is the estimated airway resistance; and Fd is the desired flow rate, with $Rh \times Fd = B$.

The equation describing the relationship between air flow rate, lung parameters, and the driving pressures is:

$$Pressure = V/C + R \times dV/dt + Pmus(t), \quad (4)$$

where: C is the lung compliance, R is the airway resistance, dV/dt is the air flow rate, and Pmus is the patient muscle effort in units of pressure.

Equating the right-hand sides of Equations 3 and 4 for the case when V is less than Vlim and when Pmus(t)=0 gives:

$$V = H \times Rh/R \times Fd(1 - exp(-t/H)),$$
and,
$$dV/dt = Rh/R \times Fd \times exp(-t/H), \quad (5)$$

where $H = R/(1/C - 1/Ch)$.

If this model fits the system behavior, setting Rh=R and Ch=C would meet the delivery requirements of a constant flow rate of magnitude Fd. However, the actual behavior will deviate from this for several reasons, which include breathing activity by the patient, inadequacy of the model of Equation 4, and errors in the delivery servo for airway pressure. The function of the adaptor unit 14 must be modified to include some form of averaging over the course of the breath to achieve the desired flow pattern.

Equation 5 can be rewritten so that dV/dt is a function of V:

$$dV/dt = -V/H + Fd \times Rh/R. \quad (6)$$

By measuring dV/dt for several values of V during the inhalation, a straight line approximation by the least square method can be made to fit the data:

$$dV/dt = m \times V + b, \quad (7)$$

where: m is the estimated value of $-1/H = (1/Ch - 1/C)/R$, and b is the estimate of $Fd \times Rh/R$.

The first stage of the adaptor unit is to adjust Ch until m=0. This is done by using the estimate of C as the value of Ch on the next breath. Equation 7 can be solved for C as follows:

$$C = 1/(1/Ch - m \times Fd \times Rh/b). \quad (8)$$

The second stage is to adjust Rh until b is equal to Fd, the desired flow rate.

If the new value of Rh is made the estimated value of R, then:

$$R = Fd \times Rh/b. \quad (9)$$

It should be noted that the mean value of dV/dt will not equal b unless m=0. Since inhale time is fixed, both Rh and Ch affect the delivered volume.

The values of coefficients A and B will be altered by the adaptor in proportion to the changes in Rh and 1/Ch. If the procedure outlined above is applied to noise-free measurements from a perfectly linear lung, the adaptation will be perfect in a single breath. However, to provide stability in the face of disturbances such as transient patient efforts, noise, and nonlinear lung behavior, the prescribed changes in A and B are reduced by a factor, Adgain, between 0 and 1.

Combining the estimate of C from Equation 8 with Equation 3 gives the new estimate of A with the adjustment factored by Adgain:

$$A(new) = A + (1/C - 1/Ch) \times Adgain. \quad (10)$$

Combining the estimate of R from Equation 9 with Equation 3 gives the new estimate of B with the adjustment factored by Adgain:

$$B(new) = B + Fd \times (R - Rh) \times Adgain. \quad (11)$$

Further limitations are placed on the changes in A and B to ensure good behavior in the presence of large, transient patient efforts. The magnitude of the change in either term is limited to a fraction of its current value. These limits are imposed on the changes before the factor of Adgain is applied. Both pressure terms are limited to minimum, nontrivial values. The sum of $A \times Vtrg$ and B is limited to the maximum pressure set by the clinician. These limits guarantee bounded pressure values in the system, regardless of the patient's behavior.

Figure 6:
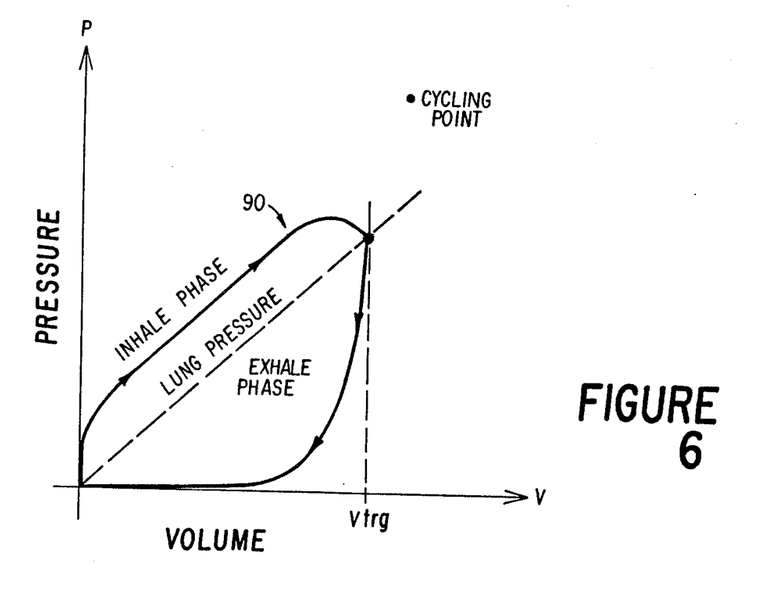
FIG. 6 shows a typical pressure-volume waveform of the control law in the ventilator in accordance with the invention.

Some salient phases in the ventilation in accordance with the preferred embodiment of the invention are now described. References are to FIGS. 5, 6 and 9.

Realizing Target Pressure

When the adaptor unit 14 computes a target, or ideal, PV waveform 90 characterizing the patient's respiratory requirements, the PV waveform 90 is used for comparison of the actual pressures and volumes in the regulator 4. The volume is monitored and measured. A target pressure corresponding to them in the regulator 4.

Patient Monitoring

While the adaptor unit 14 is computing the proper pressure-volume waveform 90 for the patient in light of the clinician's input and the monitored data on lines 7 and 9, the patient's respiratory condition is being continuously monitored. In other words, the actual pressures and volumes are determined, and the ventilation levels, such as flow, are computed therefrom. Furthermore, by measuring the rate of pressure and volume change, the patient's airway resistance and lung compliance are also computed. The information computed allows the ventilator to recognize a patient-initiated inhale or exhale cycle and to act accordingly. This information also allows an index of patient activity to be computed.

The monitored data, and the derived data computed therefrom, further allow the ventilator to recognize leaking or blockage of the patient's airways and to trigger alarms to alert the clinician in charge of the patient. The monitored and computed data are then used to adapt the PV waveform 90 for the patient.

With the above discussed principles as a background, the system in accordance with the preferred embodiment of the invention, detailed in FIG. 9, can now be described. It should be noted that although the illustrated embodiment is capable of both negative and positive transference of respiratory gas, only positive transferences, or gas delivery, will be discussed for simplicity. The discussion is equally applicable to negative tranferences, that is, exhalation or gas withdrawal.

During the course of each breath, the volume delivered is in accordance with the regulated pressure, hence the PV control law. An inhale air delivery mechanism 22 is attached to a patient 1. The delivery mechanism 22 in turn is driven by a motor 8, which generates the desired pressure in a tubing 19 to the patient 1. A pressure transducer 10 attached to the delivery mechanism 22 generates an electrical signal 7 indicating the pressure, and a shaft encoder 24 also attached thereto generates a signal 9 that is proportional to the piston position. This piston position signal 9 indicates the volume of air being delivered from the delivery mechanism 22.

A pressure target generator 12 generates a pressure target signal 18 as a function of the volume of air being delivered to the patient 1 in accordance with the PV control law. A pressure comparator 26 compares the pressure target signal 18 with a pressure return signal 29. This return signal 29 will principally be the actual pressure in the delivery mechanism, or cylinder, 22 as detected by a cylinder pressure transducer 10 and transmitted as a cylinder pressure signal 7, if an added artificial resistance from a servo resistance generator 27 is not required or present, such as when the resistance generator 27 is inoperative. Outputs from the pressure target generator 12 and the pressure return signal 29 are combined to produce an error signal 30, which is converted by drive electronics 6 into an electric motor drive current 31 to drive the motor 8. The servo system follows the PV law as described to provide well-regulated respiration gas to the patient 1.

Optimal Positive Back Pressure

Figure 7:
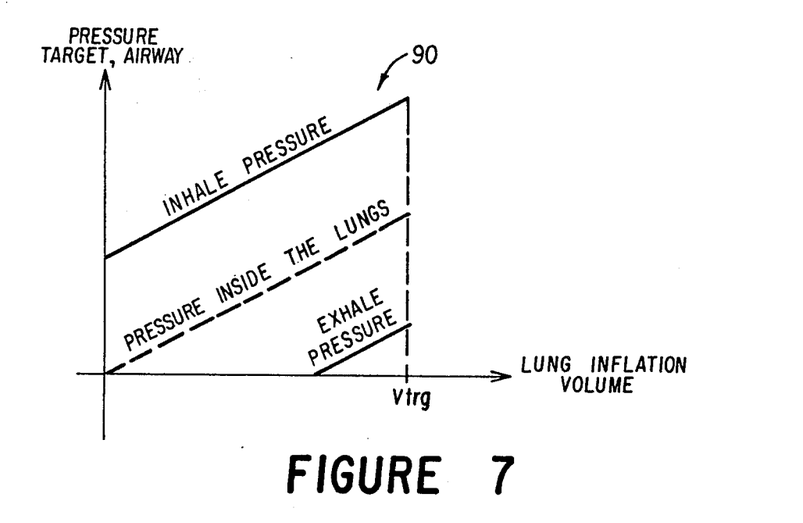
FIG. 7 shows the pressure-volume waveform for a form of the control law that provides optimal positive back pressure.

In certain disease conditions, such as emphysema, exhalation takes much longer than for persons with healthy lungs. The pressure in the thoracic cavity surrounding the airways is higher than the pressure inside the airways. Because of the diseased lungs, the walls of the airways may collapse more easily in this condition, thus limiting the maximum flow rate to an abnormally low value. Paradoxically, the maximum value of flow rate may be achieved when a certain positive pressure is applied at the airway opening. In the prior ventilation art, this is achieved by the use of a selected fixed resistance in the expiratory tubing 19. This has several disadvantages, due to the back pressure being dependent upon the expiratory flow rate. The optimal back pressure depends upon the pressure in the thoracic cavity, since it is the pressure acting across the walls of the airways that must be limited. The pressure in the thoracic cavity, in turn, depends upon the level of lung inflation, since it is due to the elastic recoil of the chest wall. Therefore, the optimal back pressure is a function of the lung volume. In the preferred embodiment, a pressure-volume servo control is imposed on the exhale cylinder 23, in the same manner as is done with the inhale cylinder 22 to achieve this optimal back pressure. One method of generating this back pressure control is illustrated in FIG. 7. The airway pressure during exhalation has the same rate of change with volume as during inhalation. It is lower than the inhale law by a fixed amount, except that it has a minimum value of zero. The fixed amount by which it is lower may be controlled by a knob on the control panel 13 of the ventilator. Alternative methods of generating a back pressure function include an independent control of the slope of the line as a function of volume. Others include generating pressure-volume laws nonlinearly or piecewise linearly. Still another method of adjusting the back pressure to maximize exhale flow rate in the ventilator controller is to do so automatically.

Negative Back Pressure

Figure 8:
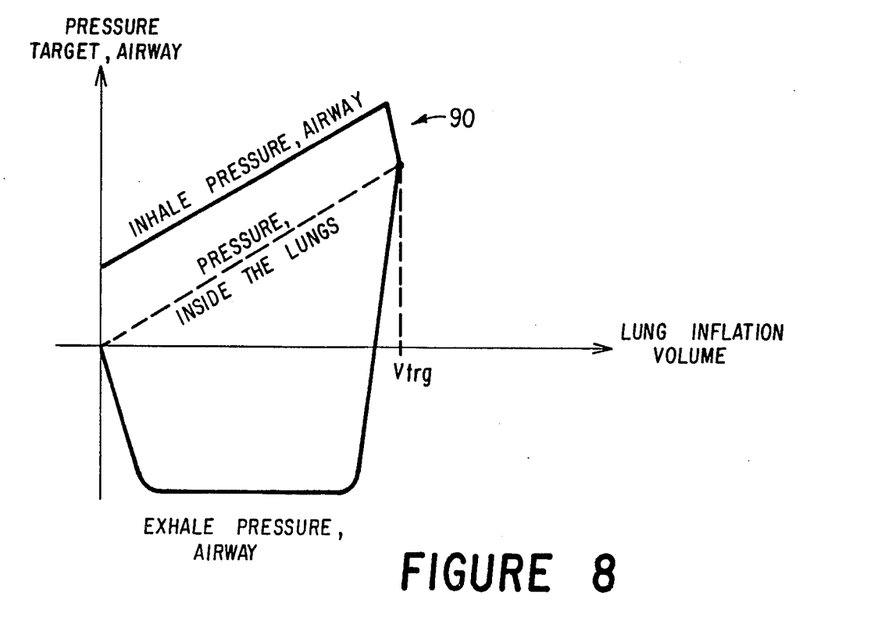
FIG. 8 shows the pressure-volume waveform of the control law that will produce an artificial cough.

The capability of supplying negative as well as positive back pressure permits an artificial cough to be produced. In the preferred embodiment, the negative pressure is servo-controlled as a function of the removed volume, as shown in FIG. 8. In this method, the volume of air that may be removed is limited by the air-moving capabilities of the ventilator hardware. This technique prevents the application of negative pressure to the lung, which might force it down to a dangerously low volume.

Added Artificial Resistance and Increased Switching Pressure

Added artificial resistance is available in the preferred embodiment. Pressures applied to the patient are modified by the resistance generator 27 in response to the flow signal input 17 and a resistance controlling input 15 emanating from the adaptor unit 14. Pressures are also modified by the adaptor unit 14 in response to the signal 45 from the patient activity detector 43. The resulting pressure target can be expressed as follows:

$$Ptarg = A \times Volume + B + Padded + Presistance, \quad (12)$$

where:

$$Padded = Radded \times Flowtarget, \quad (13)$$

$$Presistance = -Radded \times dV/dt, \quad (14)$$

$$Radded = N \times Rincrement, \quad (15)$$

and N is the number of consecutive low volume breaths due to patient activity and Rincrement is the incremental resistive amount resulting from the added resistance Radded. Flowtarget is the desired flow set by the clinician at the front panel 13. Ptarg is the difference between the signal emanating from the pressure target generator 12 on line 18 and that emanating from the resistance generator 27 on line 42 in the embodiment of FIG. 9.

In FIG. 9, the monitor unit 16 stores volume signals 9, pressure signals 7, and flow signals 17. From these signals the monitor unit 16 provides data to the patient activity detector 43 through a line 44. The patient activity detector 43 determines a measure of activity and sends this measure as a signal 45 to the adaptor unit 14. In the embodiment this measure is N, the number of consecutive low volume breaths due to patient activity. In response to the measure signal 45, the adaptor unit 14 adds to the output on an output line 18 a pressure Padded:

$$Padded = Radded \times Flowtarget. \quad (16)$$

In addition, the adaptor unit 14 sends a resistance controlling signal on a line 15 to the servo resistance generator 27 for generating a portion of the pressure target, Presistance:

$$Presistance = -Radded \times dV/dt. \quad (17)$$

Thus, for breaths with added resistance, if patient efforts cause the actual flow rate, dV/dt, to be less than the prescribed rate, Flowtarget, then the pressures to the patient are increased. Similarly, when the patient causes the actual flow rate to exceed Flowtarget, the applied pressures are diminished. When patient effort or lack of effort causes dV/dt to equal Flowtarget, the applied pressures are those of the prescribed pressure-volume waveform.

For breaths with added inhale control law resistance the pressure required to actively switch from inhale to exhale is modified as follows:

$$Pswitching = N \times Pincremental + Psw, \quad (18)$$

where N is the number of consecutive low volume breaths due to patient activity and Psw represents the lowest pressure required to actively switch. The new switching pressure must be sufficient to compensate for the added resistance and to provide an increased required effort to actively switch from inhale to exhale. With this added resistance and added required switching pressure, it is possible to apply pressures necessary to assure ventilation targets in cases where patient efforts repeatedly cause inadequate delivery volumes. This method also avoids modifying the coefficients A and B of the pressure volume control law.

Conversely, in other cases, for example where patient efforts repeatedly cause excessive delivery volumes, the added artificial resistance and pressure incremental amount discussed above can be negative amounts. Adding negative amounts effectively reduces the resistive sensation of breathing through the tubing.

Partial Assistance.

The partial assistance mode of ventilation allows the clinician to prescribe a percentage of required tidal volume to be delivered by the ventilator. The complementary fraction of the target tidal volume is first actively inspired by the patient. The effect is to have the patient initiate the breath and to begin assistance by the ventilator after a selected percent of the target voluntary tidal volume, for example, ninety percent, has been inspired. Between the selected percent, or ninety percent here, and one hundred percent of the target voluntary tidal volume, there is a smooth transition to the positive pressure-volume waveform, which is the output of the adaptor unit 14. The following equations describe the control law for this partial assistance mode, where air pressure is a function of volume for volumes ranging from zero volume to the full target tidal volume:

$$Pressure = 0, \text{ when } 0 < Volume < 0.9TVv; \quad (19)$$

$$Pressure = (A + B/TVv)(10 Volume - 9TVv), \text{ when } 0.9TVv < Volume < TVv; \text{ and} \quad (20)$$

$$Pressure = A \times Volume + B, \text{ when } TVv < Volume < TVtarget, \quad (21)$$

where:

A = the slope coefficient from Equation 1 describing the output of the adaptor unit 14, B = the offset coefficient from Equation 1 describing the output of the adaptor unit 14, TVv = the voluntary tidal volume actively inspired by the patient and defined as TVtarget × (100 − %Assist)/100, TVtarget = tidal volume as set by the clinician, and %Assist = percent assistance as set by the clinician.

Intermittent partially assisted ventilation (IPAV) is similar to IMV and SIMV. The difference is that the intermittent mandatory breaths are partially assisted as described above, with the target voluntary tidal volume now being equal to a running average of spontaneous tidal volumes. The control law for IPAV is defined as follows:

For spontaneous breaths, $$Pressure = 0, \text{ for all volumes.} \quad (22)$$

For intermittent partially assisted breaths, $$Pressure = 0, \text{ when } 0 < Volume < 0.9STV; \quad (23)$$

$$Pressure = (A + B/STV)(10 Volume - 9STV), \text{ when } 0.9STV < Volume < STV; \text{ and} \quad (24)$$

$$Pressure = A \times Volume + B, \text{ when } STV < Volume < TVtarget, \quad (25)$$

where A, B and TVtarget are defined as above, and STV is a running average value of spontaneous tidal volumes.

The variable partial assistance described above is believed to offer a method of aiding patient ventilation that is more responsive to and more comfortable for the patient, is closer to normal breathing, and also is capable of providing better ventilation-perfusion matching than the conventional ventilators in the prior art.

A more general method for providing partial assistance in accordance with the principles discussed above is to have the adaptor unit 14 modify the inputs to the pressure target generator 12 so that the area under the PV control law waveform is reduced in proportion to inputs from the front panel 13. The area under the PV control law waveform can be reduced by proportionally decreasing the value of either A or B in the following control law equation:

$$Pressure = A \times volume + B. \quad (26)$$

Figure 12A:
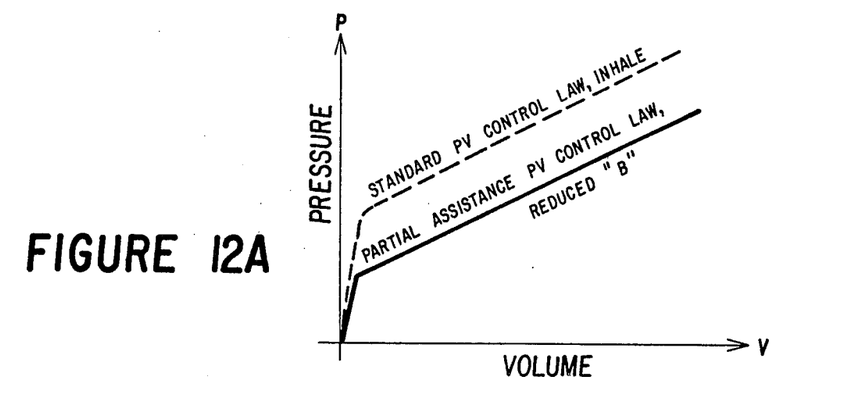
FIGS. 12A–12C show several alternative pressure-volume control laws for partial assistance.
Figure 12B:
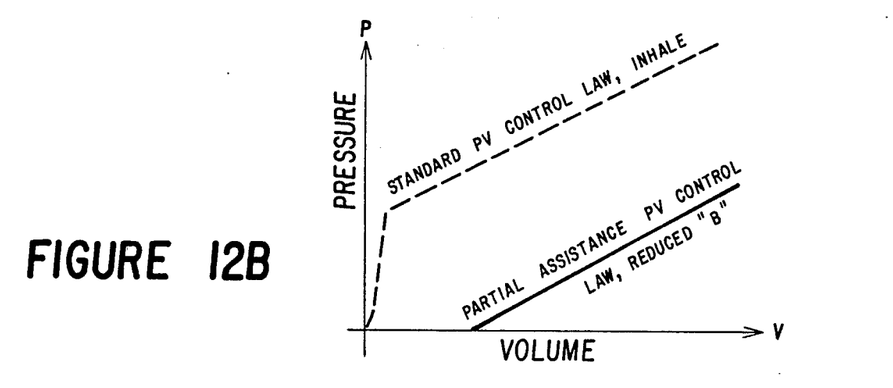
Figure 12C:
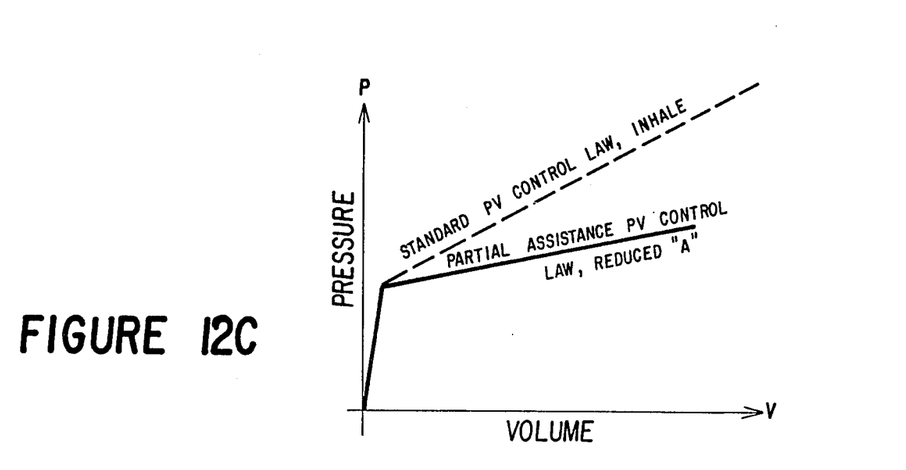

This would effectively reduce ventilator assistance throughout the breath. Examples of partial assistance control laws of this type are shown in FIGS. 12A–12C. Alternatively, the partial assistance PV control law could be the same as described above, with pressure control starting at 0 mbar for the first part of the breath and then moving to the positive pressure control law, but with the switching between the two being determined by time or flow. Again, partial assistance can be provided for all breaths or for certain selected ones.

We claim:

1. A ventilator for regulating respiration gas, comprising:

a source for transfer of respiration gas in response to a regulatory signal;

measuring means coupled to said source for measuring pressure and volume of said respiration gas being transferred by said source and for providing a pressure signal and a volume signal to represent same; and regulator means coupled to said measuring means and said source (a) for generating a pressure target from comparison of said volume signal with a pressure-volume control law, having a predetermined constant term (b) for comparison of said pressure target with said measured pressure signal, and (c) for generation of said regulatory signal to regulate, in response to said comparison of said pressure target, the pressure of said respiration gas in accordance with said pressure-volume control law.

2. The ventilator as in claim 1, wherein said regulator means comprises:
a pressure target generator coupled to said source for generating said pressure target in response to the volume of air transferred;
a pressure comparator coupled to said pressure target generator (a) for comparing said measured pressure with said pressure target and (b) for generating an error signal; and
electronic means coupled to said pressure comparator for generating said regulatory signal in response to said error signal.

3. The ventilator as in claim 1 or 2, further comprising:
an airway transducer coupled to said source for measuring the airway pressure of said respiration gas being coupled to a patient and for providing an airway pressure signal to represent same; and
a cycling logic circuit coupled to said regulator means and to said airway pressure transducer for generating, in response to a comparison of said pressure target and said airway pressure signal, a phase signal to effectuate a reversal in said transfer of said respiration gas.

4. The ventilator as in claim 3, wherein said source comprises air control valves and wherein said ventilator further comprises a valve control means coupled between said cycling logic circuit and said air control valves for switching said valves in response to said phase signal to effectuate said reversal.

5. The ventilator as in claim 3, further comprising:
an input port for receiving clinician inputs;
a monitor unit coupled to said measuring means for storing information on the observed volume and pressure during said transfer of respiration gas;
a patient activity detector coupled to said monitor unit for determining a level of patient activity; and
an adaptor unit coupled to said activity detector and said input port for generating a resistance controlling signal and an adjustment signal in response to said level of patient activity;
wherein said adjustment signal modifies said pressure target generator in subsequent breaths; and
wherein said regulator means further comprises:
a resistance generator coupled to said resistance controlling signal for generating an artificial additional pressure signal; and
combining means coupled to said artificial additional pressure signal and to said pressure target for combining said artifical additional pressure signal with said pressure target to produce said error signal.

6. The ventilator as in claim 3, further comprising:
an input port for receiving clinician inputs;
a monitor unit coupled to said measuring means for storing information on the observed volume during said transfer of respiration gas; and
an adaptor unit coupled to said input port, to said monitor unit, and to said pressure target generator for generating an adjustment signal to reduce, in response to said clinician inputs, the area under a curve representing said pressure-volume control law, thereby effectuating ventilation partial assistance.

7. The ventilator as in claim 2, further comprising:
an input port for receiving clinician input;
a monitor unit coupled to said measuring means for storing information on the observed volume during said transfer of respiration gas; and
an adaptor unit coupled to said input port, to said monitor unit, and to said pressure target generator for comparing said clinician inputs with said stored information to produce an adjustment signal representing a modified pressure-volume control law; and
wherein said adjustment signal modifies said pressure target generator in subsequent breaths.

8. The ventilator as in claim 2, further comprising:
an input port for receiving clinician inputs;
a monitor unit coupled to said measuring means for storing information on the observed volume and pressure during said transfer of respiration gas;
an adaptor unit coupled to said input port, to said monitor unit, and to said regulator means for generating a resistance controlling signal and an adjustment signal in response to said stored information and said clinician inputs; and
a differentiating unit coupled to said measuring means to produce a piston velocity signal; and
wherein said adjustment signal is coupled to said pressure target and wherein said regulator means further comprises:
a resistance generator coupled to said resistance controlling signal and said piston velocity signal for generating an artificial additional pressure signal; and
combining means coupled to said artificial additional pressure signal and said pressure target for combining said artificial additional pressure signal with said pressure target to produce said error signal, modified.

9. The ventilator as in claim 2, further comprising:
an input port for receiving clinician inputs;
a monitor unit coupled to said measuring means for storing information on the observed volume during said transfer of respiration gas;
a monitor signal coupled to said monitor unit as an output thereof and as a function of prior spontaneous tidal volumes transferred by said ventilator; and
an adaptor unit coupled to said input port and said monitor signal (a) for generating an adjustment signal for regulation in accordance to a constant airway pressure for a predetermined fraction of a breath, said fraction being in response to one of said clinician inputs and said monitor signal and (b) for generating at the termination of said predetermined fraction of a breath another adjustment signal for regulation in accordance with said pressure-volume control law.

* * * * *

UNITED STATES PATENT AND TRADEMARK OFFICE
CERTIFICATE OF CORRECTION

PATENT NO. : 4,448,192

DATED : May 15, 1984

INVENTOR(S) : Stawitcke et al.

It is certified that error appears in the above—identified patent and that said Letters Patent is hereby corrected as shown below:

Column 10, line 44, delete "them in the regulator 4." and add
-- this volume is determined in accordance with the PV waveform
90. This target pressure is compared with the actual pressure
monitoret and measured, and any deviation from the target
pressure is corrected by the electronics 6 of a servo-control
system in the regulator 4. --.

Signed and Sealed this

Twenty-third Day of April 1985

[SEAL]

Attest:

DONALD J. QUIGG

Attesting Officer

Acting Commissioner of Patents and Trademarks